(12) United States Patent
Frohliger et al.

(10) Patent No.: US 11,386,392 B2
(45) Date of Patent: *Jul. 12, 2022

(54) USER-DEFINABLE EPISODES OF ACTIVITY AND GRAPHICAL USER INTERFACE FOR CREATING THE SAME

(71) Applicant: Aver Informatics Inc., Lake De Pere, WI (US)

(72) Inventors: Matthew S. Frohliger, Green Bay, WI (US); Kurt T. Brenkus, De Pere, WI (US); Steve C. Kohlmann, Green Bay, WI (US)

(73) Assignee: Aver Informatics Inc., Lake De Pere, WI (US)

( * ) Notice: Subject to any disclaimer, the term of this patent is extended or adjusted under 35 U.S.C. 154(b) by 207 days.

This patent is subject to a terminal disclaimer.

(21) Appl. No.: 16/871,249

(22) Filed: May 11, 2020

(65) Prior Publication Data

US 2020/0342982 A1 Oct. 29, 2020

Related U.S. Application Data

(63) Continuation of application No. 13/870,760, filed on Apr. 25, 2013, now Pat. No. 10,650,116.

(51) Int. Cl.
G06Q 10/10 (2012.01)
G16H 40/20 (2018.01)

(52) U.S. Cl.
CPC .............. *G06Q 10/10* (2013.01); *G16H 40/20* (2018.01)

(58) Field of Classification Search
CPC .............................. G06Q 10/10; G16H 40/20
See application file for complete search history.

(56) References Cited

U.S. PATENT DOCUMENTS

| 5,970,463 | A | 10/1999 | Cave et al. |
| 7,676,379 | B2 | 3/2010 | Kil et al. |
| 8,121,869 | B2 | 2/2012 | Dang |
| 8,271,298 | B2 | 9/2012 | Ruben et al. |
| 8,315,890 | B2 | 11/2012 | Lynn et al. |
| 8,630,871 | B2 | 1/2014 | Rastogi |
| 10,650,116 | B2 | 5/2020 | Frohliger et al. |

(Continued)

OTHER PUBLICATIONS

Search Report for International Application No. PCT/US14/35571 dated Sep. 9, 2014 (8 pages).

(Continued)

*Primary Examiner* — Eliza A Lam
(74) *Attorney, Agent, or Firm* — Michael Best & Friedrich LLP

(57) ABSTRACT

Methods and systems for generating episodes of activity, such as episodes of care. One method includes generating, by a processor, a graphical user interface for display to a user. The method also includes receiving, by a processor, (1) a first selection of a trigger event for an episode of care from the user through the graphical user interface, (2) a second selection of at least one time period for the episode of care from the user through the graphical user interface, and (3) a third selection of at least one claim category for the episode of care from the user through the graphical user interface. The method further includes creating, by the processor, parameters for the episode of care based on the first, second, and third selections, wherein the parameters are applied to a plurality of medical claims to group at least two of the plurality of medical claims.

20 Claims, 15 Drawing Sheets

(56) References Cited

U.S. PATENT DOCUMENTS

| | | |
|---|---|---|
| 2002/0165738 A1 | 11/2002 | Dang |
| 2004/0143460 A1 | 7/2004 | Marhaver |
| 2005/0278196 A1 | 12/2005 | Potarazu |
| 2008/0195420 A1 | 8/2008 | Rameison et al. |
| 2009/0198517 A1 | 8/2009 | Ruben |
| 2010/0305971 A1 | 12/2010 | McLaren et al. |
| 2012/0078665 A1 | 3/2012 | Johnson et al. |
| 2012/0173273 A1 | 7/2012 | Ashford |
| 2012/0191476 A1 | 7/2012 | Reid |
| 2013/0035960 A1 | 2/2013 | Lynn et al. |
| 2014/0249848 A1 | 9/2014 | Averill |

OTHER PUBLICATIONS

Written Opinion for International Application No. PCT/US14/35571 dated Sep. 9, 2014 (5 pages).

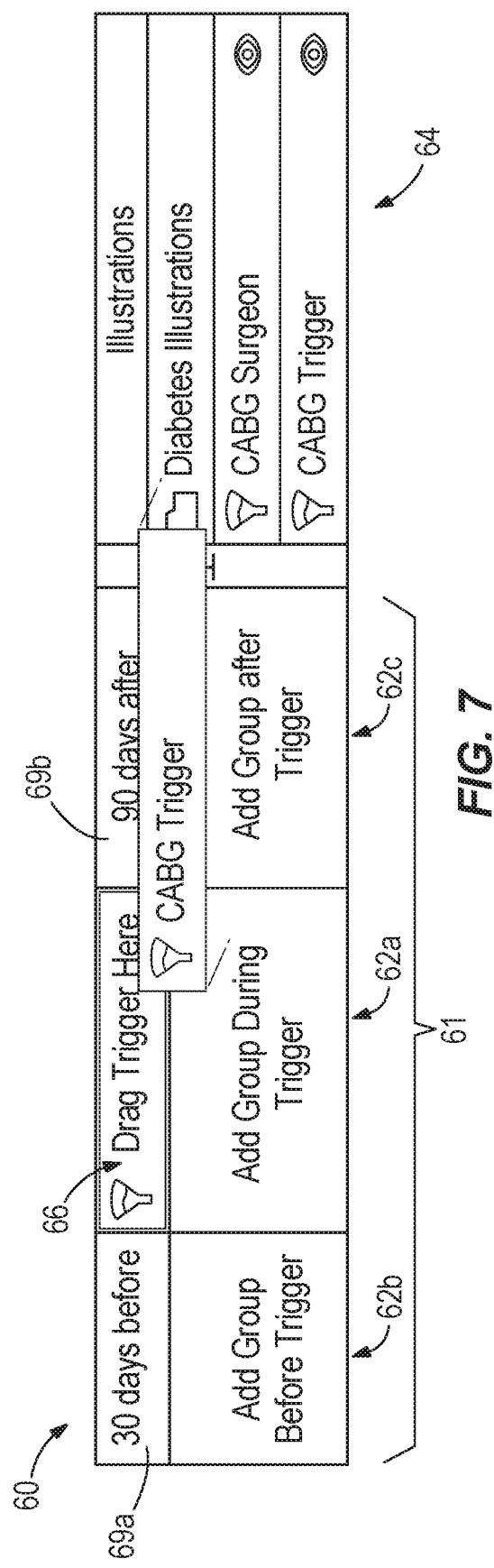
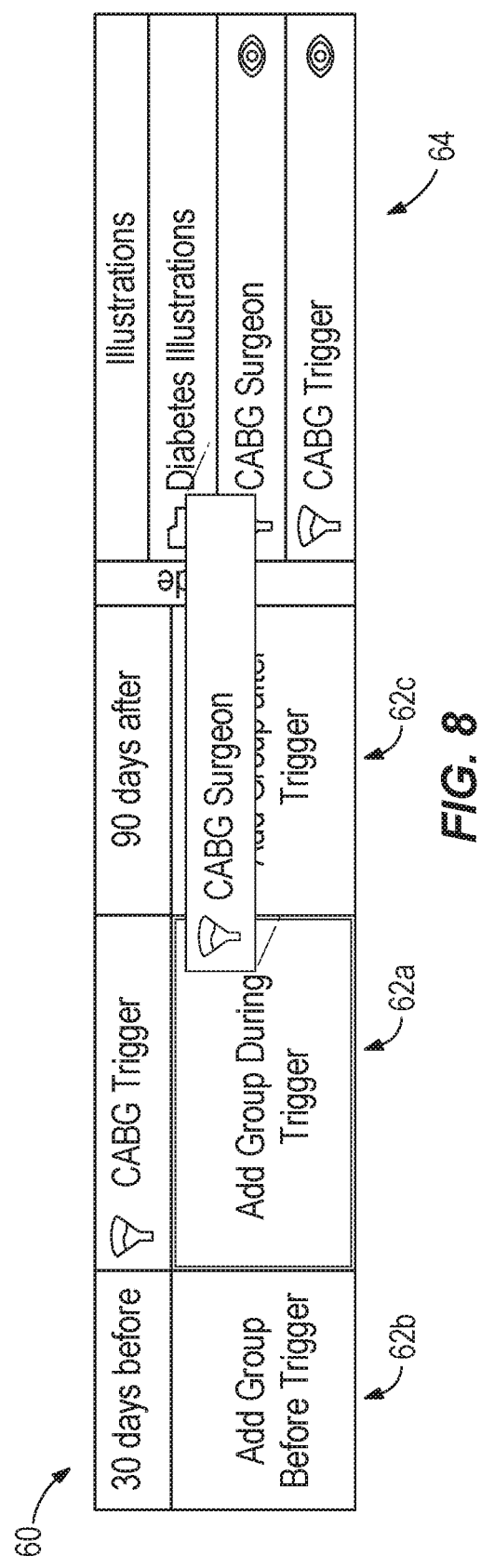
FIG. 7
FIG. 8

USER-DEFINABLE EPISODES OF ACTIVITY AND GRAPHICAL USER INTERFACE FOR CREATING THE SAME

RELATED APPLICATIONS

This application is a continuation of U.S. patent application Ser. No. 13/870,760 filed Apr. 25, 2013, the entire content of which is incorporated herein by reference.

FIELD

Embodiments of the invention relate to processing medical claims and other time-based data sets. More particularly, certain embodiments of the invention relate to manually-defining an episode of care.

BACKGROUND

Medical claim processing and analysis has become increasingly complex for a number of reasons. To aid claim analysis and processing, it is possible to bundle related medical claims into an "episode" or "episode of care." Each episode includes one or more claims for the same patient for related care (e.g., an office visit, a procedure, and a follow-up) administered to the patient within a specified period of time. Grouping claims into episodes of care can reduce the complexity of billing and claims processing. Episodes of care can also be used to provide a more efficient form of quality control for healthcare administration.

SUMMARY

Existing systems that identify episodes of care use pre-defined rules or criteria for establishing the episodes. Accordingly, users cannot modify or view the definition of a particular episode, which makes it expensive and difficult (if not impossible) to modify the system to deviate from defined standards.

Accordingly, embodiments of the present invention allow a user to manually define an episode of care. By manually-defining an episode, organizations are able to more rapidly (and more cost-effectively) define episodes that do not conform to established standards and transition to new standards. Manual-definition of episodes of care also increases transparency and efficiency. In addition to defining episodes of care, embodiments of the invention allow a user to manually define parameters for grouping other time-based data sets, in which there may be a series of related events occurring over a period of time. In these situations, instead of episodes of care, episodes of activity are defined, and the user can use similar methods and systems (e.g., a similar graphical user interface) to define parameters for the episode of activity.

In particular, one embodiment of the invention provides a method of processing medical claims. The method includes generating, by a processor, a graphical user interface for display to a user. The method also includes receiving, by a processor, (1) a first selection of a trigger event for an episode of care from the user through the graphical user interface, (2) a second selection of at least one time period for the episode of care from the user through the graphical user interface, and (3) a third selection of at least one claim category for the episode of care from the user through the graphical user interface. The method further includes creating, by the processor, parameters for the episode of care based on the first, second, and third selections, wherein the parameters are applied to a plurality of medical claims to group at least two of the plurality of medical claims.

Another embodiment of the invention provides a system for processing medical claims. The system includes a computing device including non-transitory computer readable medium storing at least one application, and a processor. The processor is configured to execute the at least one application to generate a graphical user interface for display to a user, receive, from the user, a first selection of a trigger event for an episode of care through the graphical user interface, receive, from the user, a second selection of at least one time period for the episode of care through the graphical user interface, receive, from the user, a third selection of at least one claim category for the episode of care through the graphical user interface, and generate parameters for the episode of care based on the trigger event, the at least one claim category, and the at least one time period.

Other aspects of the invention will become apparent by consideration of the detailed description and accompanying drawings.

BRIEF DESCRIPTION OF THE DRAWINGS

FIG. 7 is a screen shot illustrating a user interface for selecting a trigger event for an acute episode of care.

FIG. 8 is a screen shot illustrating a user interface for adding a claim category to an acute episode of care.

DETAILED DESCRIPTION

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways. Also, it is to be understood that the phraseology and terminology used herein are for the purpose of description and should not be regarded as limiting. The use of "including," "comprising," or "having" and variations thereof herein are meant to encompass the items listed thereafter and equivalents thereof as well as additional items. Unless specified or limited otherwise, the terms "mounted," "connected," "supported,"

and "coupled" and variations thereof are used broadly and encompass both direct and indirect mountings, connections, supports, and couplings.

In addition, it should be understood that embodiments of the invention may include hardware, software, and electronic components or modules that, for purposes of discussion, may be illustrated and described as if the majority of the components were implemented solely in hardware. However, one of ordinary skill in the art, and based on a reading of this detailed description, would recognize that, in at least one embodiment, the electronic based aspects of the invention may be implemented in software (e.g., stored on non-transitory computer-readable medium). As such, it should be noted that a plurality of hardware and software based devices, as well as a plurality of different structural components may be utilized to implement the invention.

Furthermore, it should be understood that embodiments of the invention provide methods and systems for allowing a user to manually-define parameters for grouping other time-based data sets, in which there may be a series of related events occurring over a period of time. Therefore, although the following paragraphs describe methods and systems for grouping medical claims into episodes of care, grouping medical claims is just one example of how the disclosed systems and methods can be used to group related data sets based on manually-defined parameters and other applications of the methods and systems are possible. In these situations, instead of episodes of care, episodes of activity are defined, and the user can use similar methods and systems (e.g., a similar graphical user interface) to define parameters for the episode of activity.

Figure 1:
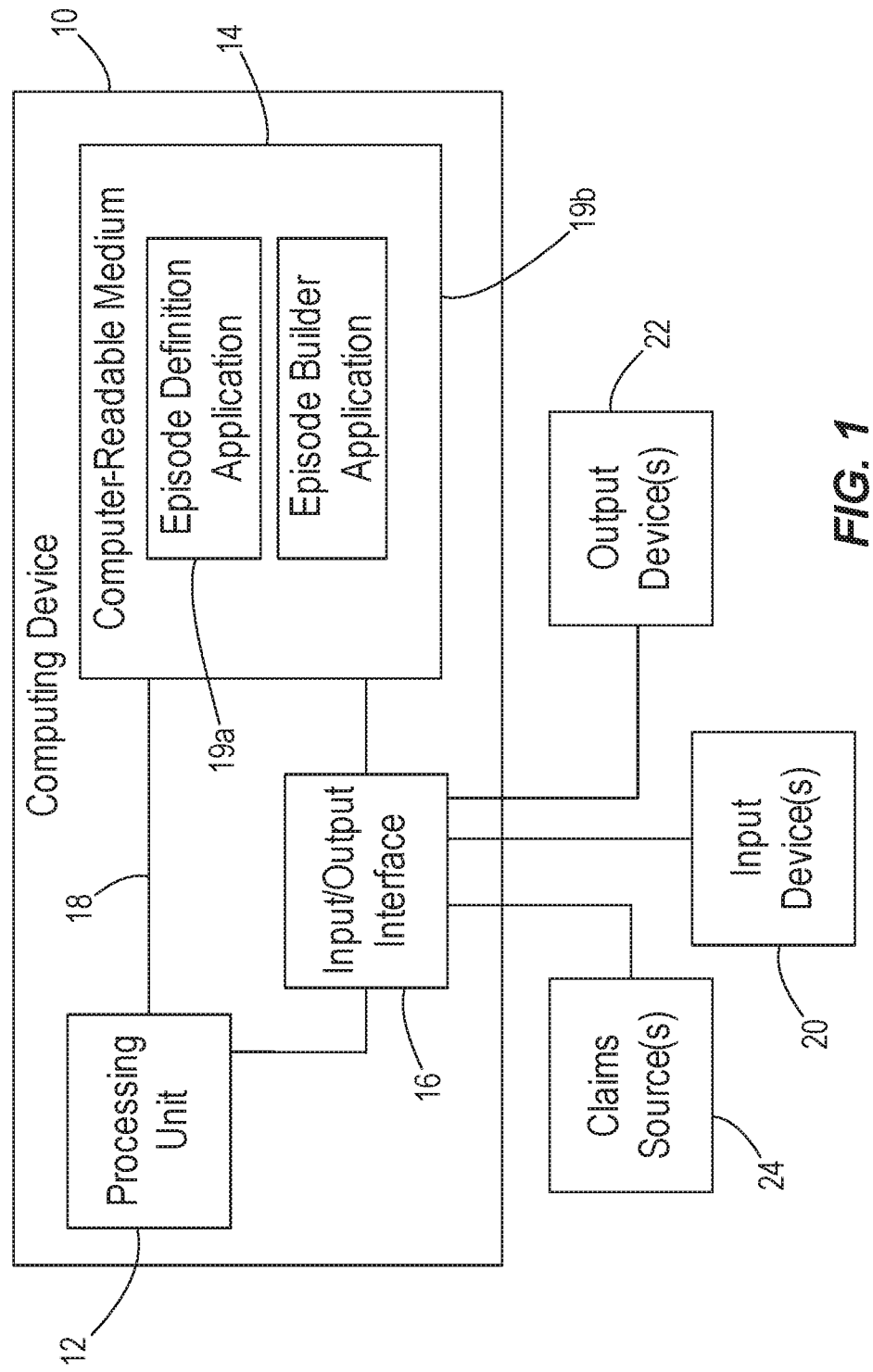
FIG. 1 illustrates a system for processing medical claims according to one embodiment of the invention.

FIG. 1 illustrates a system for processing medical claims. The computing device 10 can include a laptop computer, desktop computer, tablet computer, smart phone, smart television, a server, or other device capable of executing instructions stored in computer-readable medium. As illustrated in FIG. 1, the computing device 10 includes a processing unit 12 (e.g., a microprocessor, a microcontroller, or another suitable programmable device), non-transitory computer-readable medium 14, and an input/output interface 16. The processing unit 12, the medium 14, and the input/output interface 16 are connected by one or more control and/or data buses (e.g., a common bus 18). It should be understood that in other constructions, the computing device 10 includes additional, fewer, or different components.

The computer-readable medium 14 stores program instructions and data and, in particular, stores an episode definition application 19a. As described in more detail below, the processing unit 12 is configured to retrieve the episode definition application 19a from the medium 14 and execute the application 19a to generate a graphical user interface that allows a user to manually define an episode of care. In some embodiments, the computer-readable medium 14 also stores an episode builder application 19b. As described in more detail below, the processing unit 12 is configured to retrieve the episode builder application 19b from the medium 14 and execute the application 19b to apply parameters (i.e., generated based on user selections received by the episode definition application 19a) to a plurality of medical claims to group two or more of the claims and, consequently, the events associated with the claims, into an episode of care. It should be understood that in some embodiments, the applications 19a and 19b are combined as one application and, in other embodiments, the functionality of the applications 19a and 19b is distributed among additional applications or modules stored in the medium 14 or a separate computer-readable medium (e.g., internal to or external to the computing device 10).

The input/output interface 16 transmits data from the computing device 10 to external systems, networks, and/or devices and receives data from external systems, networks, and/or devices. The input/output interface 16 can also store data received from external sources to the medium 14 and/or provide the data to the processing unit 12. As illustrated in FIG. 1, the input/output interface 16 communicates with at least one input device 20. The input device 20 can include a keyboard, a joystick, a mouse, a touchscreen, a trackball, tactile buttons, etc. The input device 20 can be connected to the computing device 10 via one or more wired connections (e.g., a universal serial bus ("USB") cable) and/or wireless connections. Also, in some embodiments, when the computing device 10 includes a server that hosts one or both of the applications 19a and 19b, the input device 20 includes a computing device that accesses the server over at least one network (e.g., a local area network ("LAN") or the Internet).

The input/output interface 16 also communicates with at least one output device 22. The output device 22 can include at least one monitor or screen (e.g., a liquid crystal display ("LCD") monitor) that displays a graphical user interface to a user. As described above for the input device, the output device 22 can be connected to the computing device 10 via one or more wired connections, wireless connections, wired networks, and/or wireless networks. It should also be understood that in some embodiments a device can be connected to the input/output interface 16 that operates as both an input device 20 and an output device 22. For example, a touchscreen can be used that displays a graphical user interface to an operator and receives selections from the user through the interface. In addition, when the computing device 10 operates as a server that hosts one or both of the applications 19a and 19b, devices accessing the server operate as both an input device 20 and an output device 22.

As illustrated in FIG. 1, in some embodiments, the input/output interface 16 is also in communication with at least one source of claim data 24. The claim data includes medical claims submitted by one or more healthcare providers or organizations for healthcare provided to patients. Each claim can include a category or code for classifying the claim, such as an International Classification of Disease ("ICD") code and/or a Current Procedure Terminology ("CPT") code. It should be understood that in some embodiments, claims do not include an ICD or CPT code. For example, retail pharmacy claims or employment lab tests may not include such codes. Instead, different or no codes are included. Each claim can also include patient data (e.g., name, unique identifier, etc.) and time data. The time data can indicate the date or dates of care provided to the patient.

As described above, an episode of care consists of one or more related claims or events for the same patient within a specified period of time. For example, a patient may undergo heart surgery on Jan. 1, 2013 but may have laboratory work performed as a pre-condition to the surgery on Dec. 20, 2012 and may have physical therapy performed after the surgery on Jan. 15, 2013. During this time period, the patient may also receive care unrelated to the surgery, such as an emergency room visit for a sprained ankle on Dec. 30, 2013. The episode of care associated with the surgery would ideally include only those claims relating to the laboratory work, the surgery, and the physical therapy. The emergency room visit would ideally be associated with a separate episode of care.

Each episode of care includes a "trigger event." The trigger event identifies the existence of an episode (i.e., its existence prompts the creation of an episode). Claims relating to a trigger event may include specific codes, such as an ICD code, a CPT code, or a combination thereof. However, it should be understood that in some embodiments, the trigger event does not include such a code. Also, the trigger event can be based on other factors than just a claim or a code, such as patient history, previous claims or events, cost, etc. For example, a user can build an episode around a high cost service (e.g., the trigger event would be any claim or bill amount greater than a predetermined value, such as $50,000). In the above example, the claim for the heart surgery would likely be considered the trigger event and would be associated with an episode of care relating to the surgery.

Figure 2:
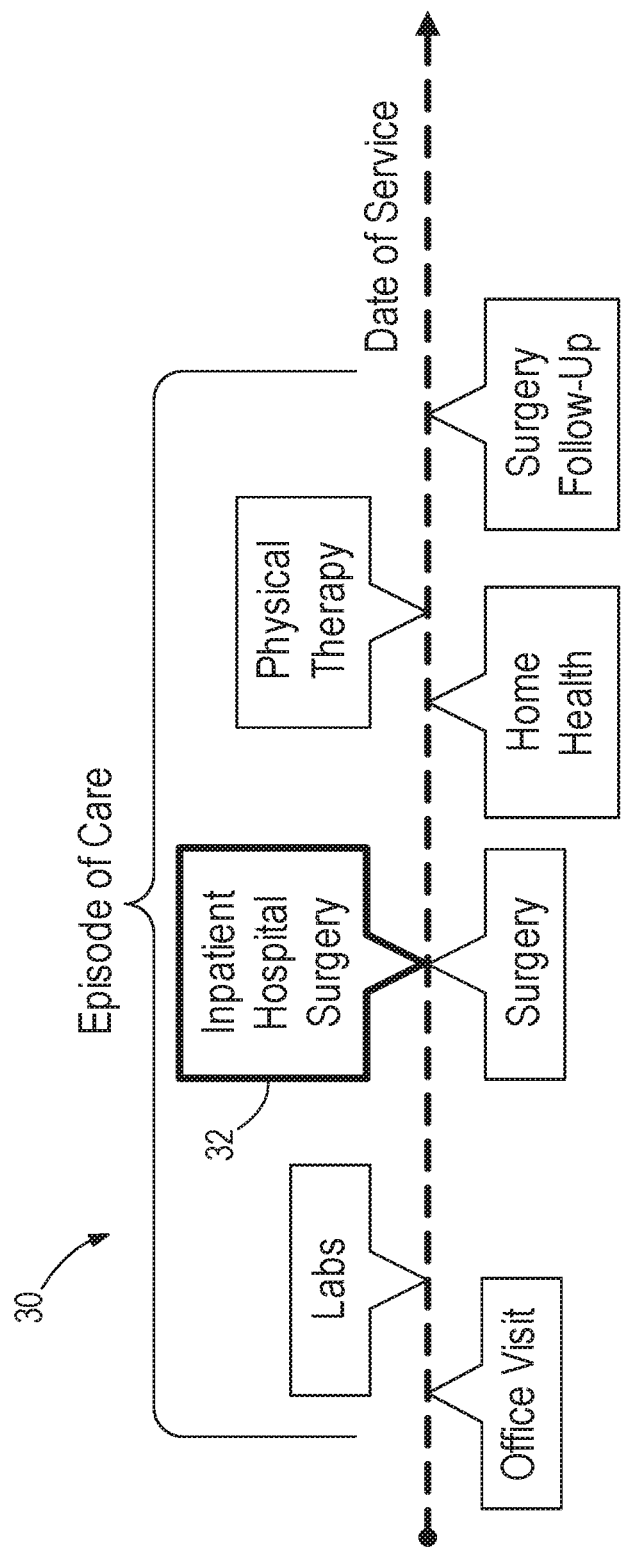
FIG. 2 illustrates an acute episode of care.

For health-related events, there are, in general, two types of episodes: (1) acute and (2) chronic. FIG. 2 illustrates an acute episode of care 30. An acute episode of care 30 includes a single trigger 32 event, which is associated with an event time window (e.g., a start time and an end time and/or a time period). An acute episode of care 30 can also include at least one of a "before" window and an "after" window. The before window includes a period of time occurring before the start of the trigger event window and the after window includes a period of time occurring after the end of the trigger event window. In some embodiments, an acute episode can include multiple before windows and/or multiple after windows. For example, an acute episode can include a first after window associated with zero to thirty days after the trigger event window and a second after window associated with thirty-one to ninety days after the trigger event window.

Figure 3:
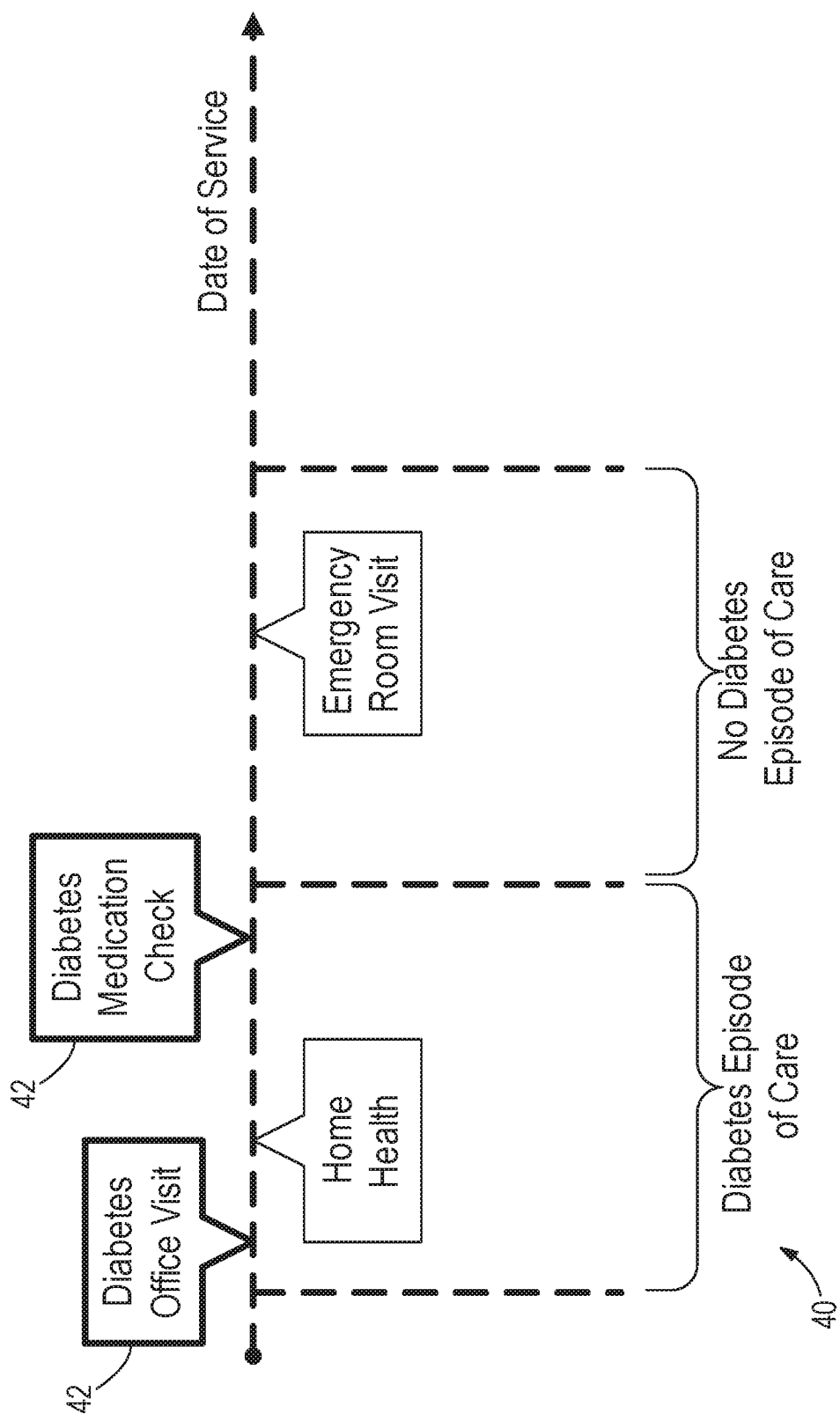
FIG. 3 illustrates a chronic episode of care.

FIG. 3 illustrates a chronic episode of care 40. A chronic episode of care 40 includes at least one trigger event 42 and an episode time window defined by a start date and a repeat period. Chronic episodes 40 are created if at least one trigger event is found within the episode time window. In some embodiments, additional trigger events within a chronic episode of care during the episode time window do not result in additional episodes. For example, the chronic episode 40 illustrated in FIG. 3 may include a "Diabetes Office Visit/Medication Check" as a trigger event, a "January 1" start date, and a "Quarterly" repeat period. Therefore, each chronic episode is associated with a 3-month period starting January $1^{st}$, April $1^{st}$, July $1^{st}$, or October $1^{st}$. Accordingly, if a patient has a "Diabetes Office Visit" claim on January $15^{th}$ and a "Diabetes Medication Check" claim on February $15^{th}$, these claims would be included in the same chronic episode of care. Similarly, because no "Diabetes Office Visit" or "Diabetes Medication Check" claim occurs in the second quarter of the year (i.e., April $1^{st}$ through June $30^{th}$), no chronic episode of care is created for the second quarter. Also, a trigger event for a chronic episode may not be related to a specific claim, but instead to a patient. For example, in some cases a patient who is diabetic could have a chronic episode even if they do not have claims specifically dealing with diabetes.

Figure 4:
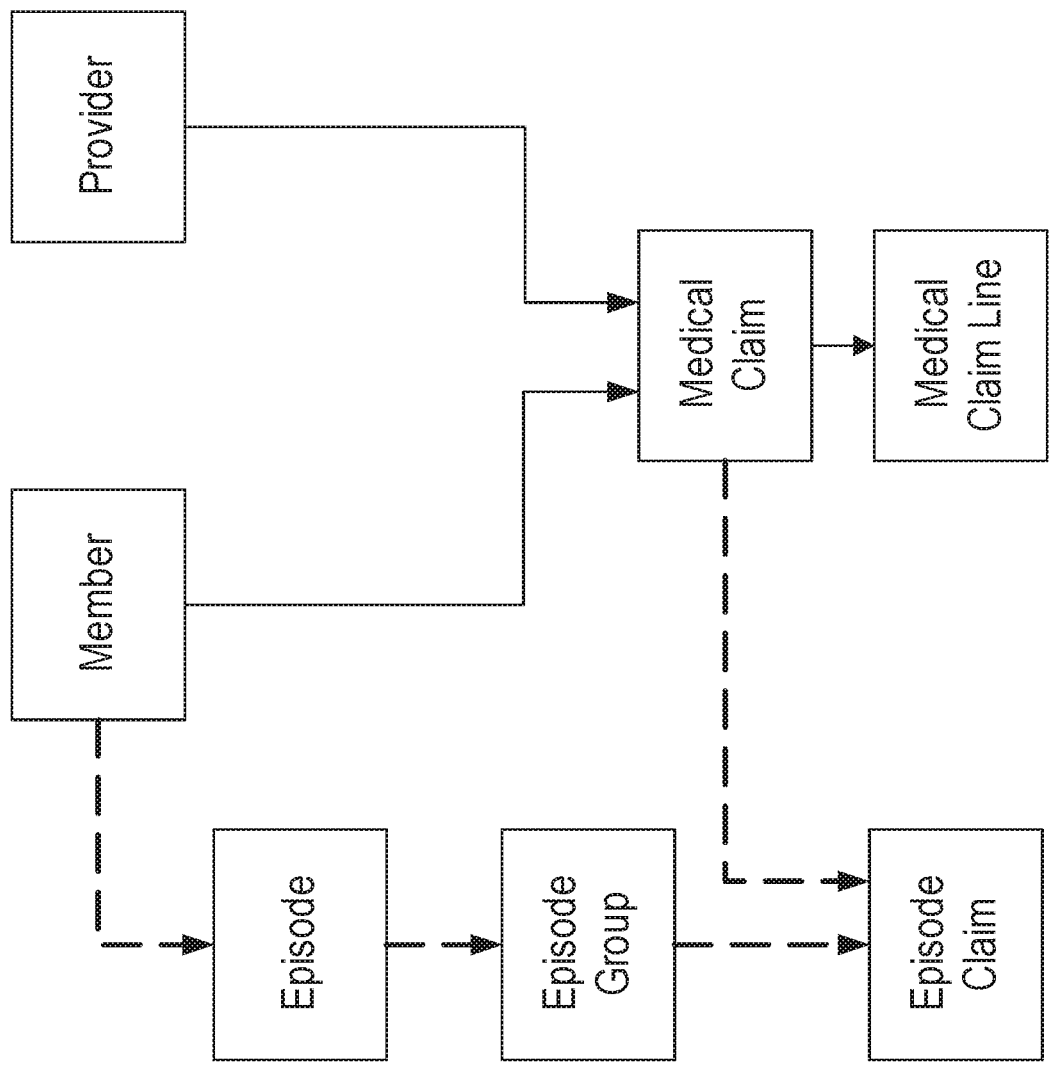
FIG. 4 schematically illustrates a relationship between episodes of care and medical claims.

FIG. 4 illustrates the relationship between episodes of care and medical claims. As illustrated in FIG. 4, episodes of care group related claims or associated healthcare records of a particular member (i.e., a patient). In particular, each episode connects a main or parent record (i.e., the record associated with the trigger event) to one or more subsidiary or child records, even if the child record is not an immediate child record to the parent record. Each episode can also define one or more claim categories connected by the episode. The claim categories define the types of claims that should be grouped within the episode. For example, an episode of care can be defined to only group claims falling within particular categories (e.g., laboratory, office visits, procedures, ambulance, physical therapy, etc.). Accordingly, the episodes do not blindly group all claims occurring within a predetermined time period. Rather, the claim categories indicate the types of claims that should be grouped within the episode. In particular, an episode may not have a category or categories associated with relating to ambulatory services or emergency room visits. Therefore, the definition of the episode would not include these claim categories.

Figure 5A:
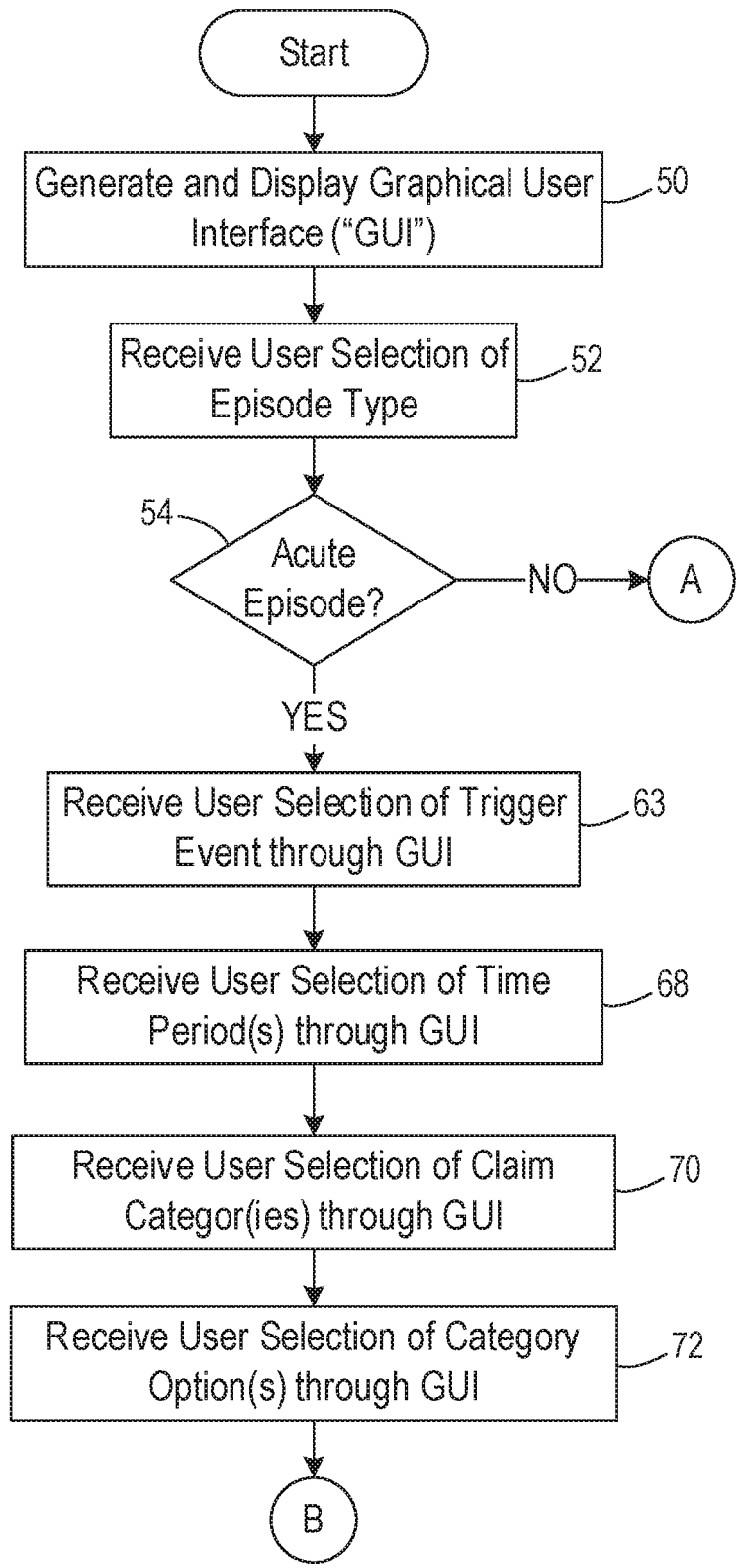
FIGS. 5a and 5b are flow charts illustrating a method of processing medical claims.
Figure 5B:
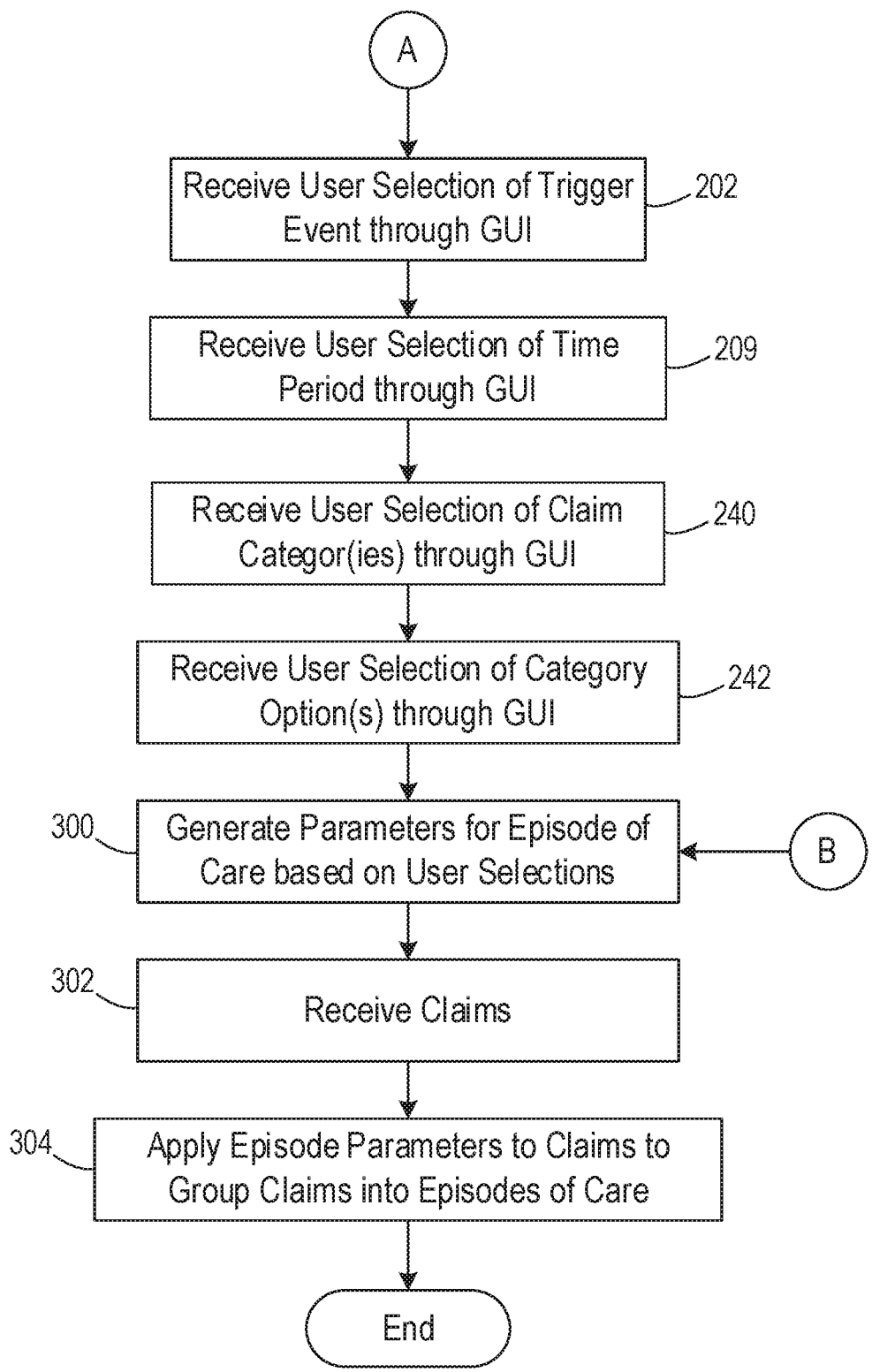

FIGS. 5a and 5b illustrates a method of processing medical claims. The method illustrated in FIGS. 5a and 5b can be performed by the processing unit 12 executing the episode definition application 19a and/or the episode application 19b. It should be understood that the functionality described below with respect to the method illustrated in FIGS. 5a and 5b can be combined and distributed between the applications 19a and 19b and additional modules or applications in various configurations. Also, any sequence implied by the method is provided merely for ease of explanation, and, it should be understood that, unless explicitly noted, no specific order of the method is required.

As illustrated in FIG. 5a, the processing unit executes the episode definition application 19a to generate a graphical user interface ("GUI") (at 50) that is displayed to a user on an output device 22, such as a monitor or display. As described in more detail below, the GUI allows the user to manually-define an episode of care. In some embodiments, a user initially uses the GUI to select a type of episode of care the user wants to define (at 52). For example, a user can select whether to define an acute episode of care or a chronic episode of care. It should be understood that in some embodiments a user can use the same GUI to define either an acute episode of care or a chronic episode of care, such that the user does not need to initially select a type of episode.

Figure 6:
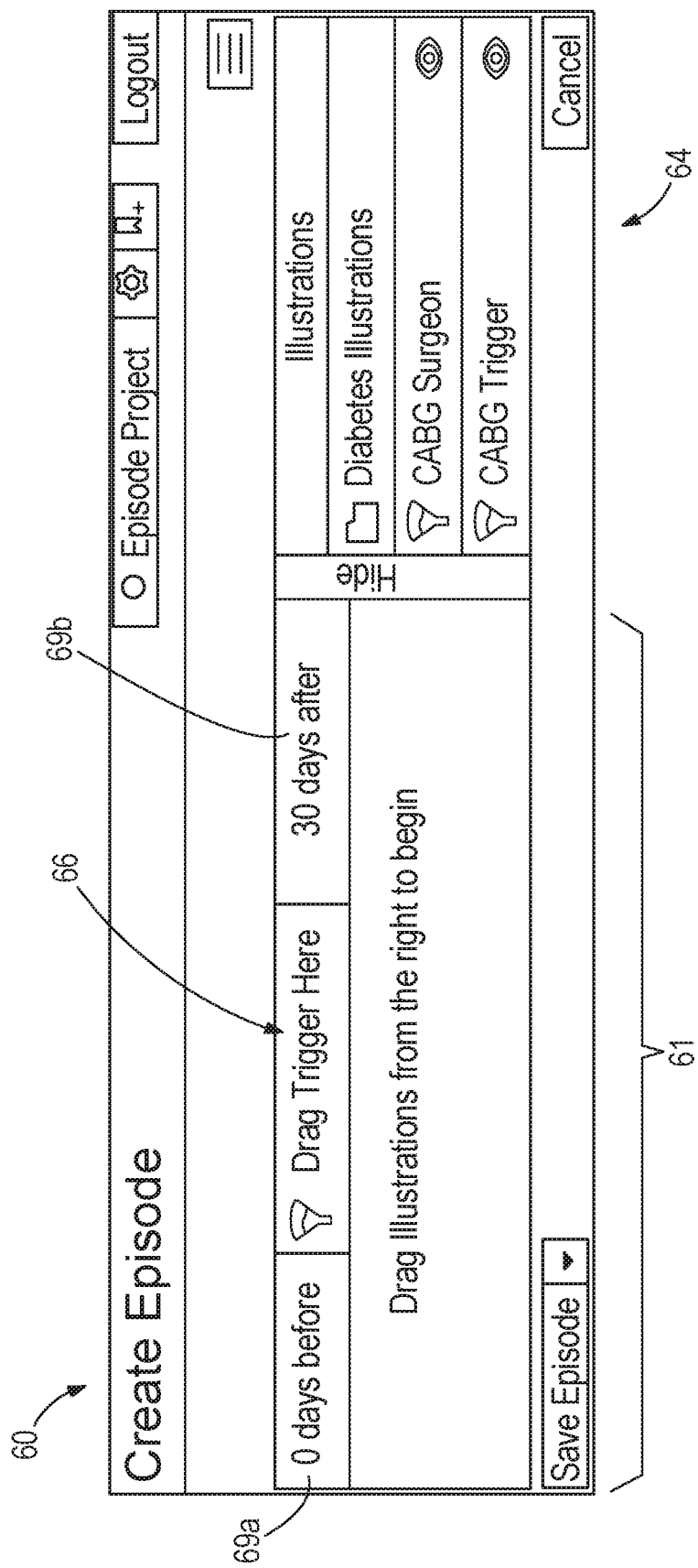
FIG. 6 is a screen shot illustrating a user interface for creating an acute episode of care.

If the user selects to manually-define an acute episode of care (at 54), the GUI displays options to the user for defining an acute episode of care. For example, FIGS. 6 and 7 illustrate portions of a GUI 60 for defining an acute episode of care. As illustrated in FIG. 7, the GUI 60 includes a graphical timeline 61 for defining an episode of care. The timeline 61 includes a trigger event window 62a, and at least one of a before window 62b associated with a time before the trigger event window 62a and an after window 62c associated with a time after the trigger event window 62a. The user uses the windows 62a, 62b, and 62c to manually define the episode of care. For example, as described below in more detail, the GUI 60 allows a user to modify the time period associated with the windows 62a, 62b, and 62c, add a trigger event to the timeline 61, and add one or more claim categories to the timeline 61. As described in more detail below, in some embodiments, the timeline 61 includes multiple before windows 62b and/or multiple after windows 62c.

The user uses the GUI 60 to add a trigger event to the acute episode of care (at 63). For example, in some embodiments, the GUI 60 allows the user to select (e.g., click on) an illustration or icon from a list 64. The list 64 includes a plurality of icons representing different types of claims (e.g., different types of healthcare events). In particular, each icon can include a textual description of a claim type (e.g., coronary artery bypass graft ("CABG") Surgeon," "Diabetes Office Visit," etc.). In some embodiments, each type of claim represented by an icon is associated with a unique classification or code, such as an ICD and/or a CPT code. Therefore, by selecting a particular icon as a trigger event, the user is selecting the unique classification or code associated with the icon as representing the trigger event. Accordingly, as described in greater detail below, the acute episode of care will be created when a claim is received that includes a code matching the unique code selected by the user. It should be understood that in some embodiments the trigger event is associated with other identifying information than medical code and/or a different event that a claim. For example, the trigger event can include a payment of a claim, a scheduled appointment date, a request for a patient's medical records, etc.

In addition to selecting the trigger event, the user can define filtering logic for the trigger event. The filtering logic defines requirements or criteria for the trigger event. The filtering logic can define one or more multiple requirements for the trigger event. For example, a user can add filtering logic to a trigger event to require that the claim associated with the trigger event have a predefined relationship with another claim (e.g., a CABG surgery claim following a laboratory claim), be associated with a particular bill amount, etc. In some embodiments, a user can select the filtering logic from list 64 (e.g., through the selection of one more icons). Alternatively or in addition, a user can manually input or define the filtering logic.

In some embodiments, the list 64 can be prepopulated with the icons. In some embodiments, a user can also manually add an icon to the list 64 (e.g., by entering a unique code or classification, a start and end time or a time period, and a description or name for the icon). In some embodiments, the user can also search or sort the list 64 (e.g., using expandable and collapsible folders) to identify a desired icon.

As illustrated in FIG. 7, after selecting an icon from the list 64 for the trigger event and/or associated filtering logic, the user can drag the selected icon to a trigger drop area 66 of the timeline 61. In particular, as illustrated in FIG. 7, if the user wants to define an episode of care where the trigger event is a coronary artery bypass graft ("CABG") surgery, the user selects an icon labeled "CABG Trigger" from the list 64 and drags the icon to the trigger drop area 66. In some embodiments, the trigger drop area 66 changes (e.g., color) when the user hovers an icon over the area 66. The change in color provides a signal to the user of when he or she can release or drop the icon to set the trigger event for the episode of the care.

The selected trigger event can define the time period for the trigger event window 62a of the timeline 61. For example, in some embodiments, a selected trigger event is associated with a predetermined start time and a predetermined end time (e.g., a predetermined number of days) that is used to set the time period for the trigger event window 62a. In particular, a 5-day inpatient stay can result in a trigger event window 62a with a time period of five days and a 7-day inpatient stay can result in a trigger event window 62a with a time period of seven days. In other embodiments, the trigger event window 62a can automatically be initially set to a default time period (e.g., 30 days). However, in some embodiments, the user can manually define this time period. For example, a user can select the trigger drop area 66 (e.g., by double-clicking on the area 66 after an icon is dropped in the area) and select a time period (e.g., from a menu or by manually entering a value).

Similarly, the user can select a time period for the before window 62b and/or the after window 62c. In some embodiments, one or both of these windows 62b and 62c default to a predetermined value (e.g., 30 days). In other embodiments, the windows 62b and 62c can be set to a time period based on the trigger event. However, the user can also manually select a time period for one or both of the windows 62b and 62c through the GUI 60 (at 68). In particular, as illustrated in FIG. 7, the timeline 61 provided through the GUI 60 includes at least one "before" window indicator 69a and at least one "after" window indicator 69b. To select a time period for a particular window, the user selects (e.g., double-clicks) the corresponding indicator and selects a new time period (e.g., as a selection from a menu or through direct data entry). In some embodiments, the user can also select a time period for a particular window by expanding or reducing the size of the window displayed within the timeline 61 (e.g., by clicking and dragging). Also, in some embodiments, a user can also use the GUI 60 to manually add additional before windows and/or additional after windows for a particular episode of care.

The user can also use the GUI 60 to add claim categories for the episode of care (at 70). As noted above, the claim categories define the type of claims that can be added to the episode. Therefore, the claim categories act as a filter for claims falling within the time periods of the episode of care. In particular, a patient may have a "Diabetes Medication Check" claim dated January 15$^{th}$ that results in the creation of an episode of care having a time period of three months. The definition of the episode of care, however, may specify that only claims falling within an "Office Visit" category or a "Laboratory" category should be grouped within the episode. Therefore, if the patient has a "Laboratory" claim dated within the three-month time period of the episode, the claim will be added to the episode. However, if the patient has an "Emergency Room Visit" claim also dated within the three-month time period of the episode, this claim will not be added to the episode. Accordingly, claim categories defined for a particular episode of care prevent the episode from blindly grouping all claims occurring within a predetermined time period.

Figure 9A:
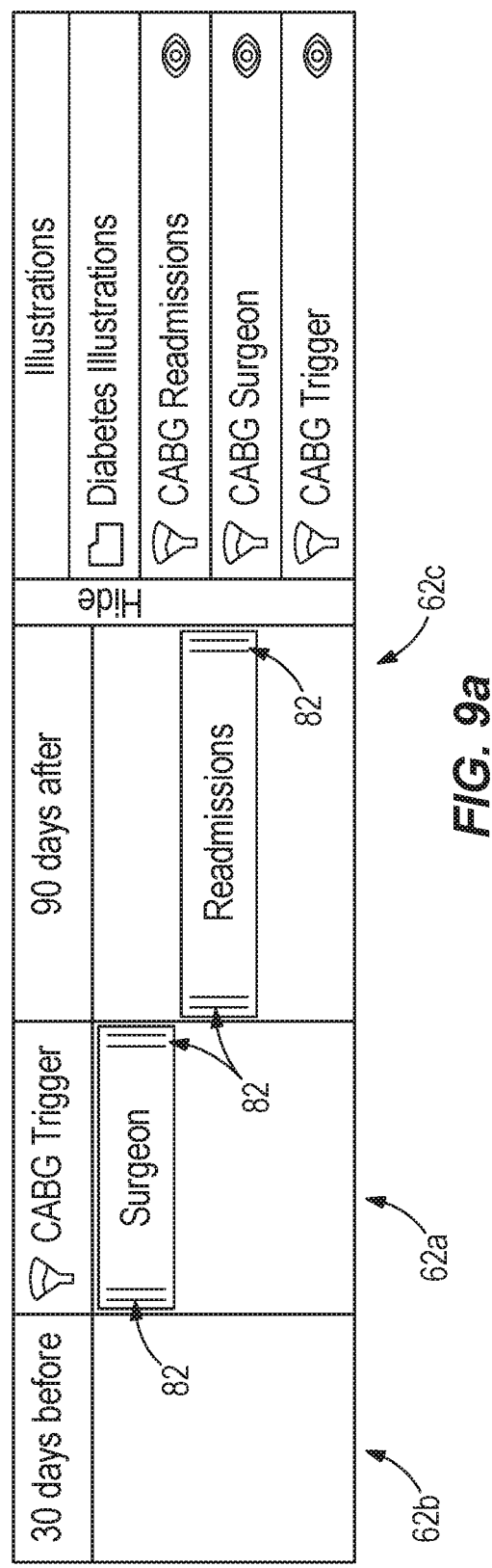
FIGS. 9a and 9b are screen shots illustrating user interfaces displaying an acute episode of care including a plurality of claim categories.
Figure 9B:
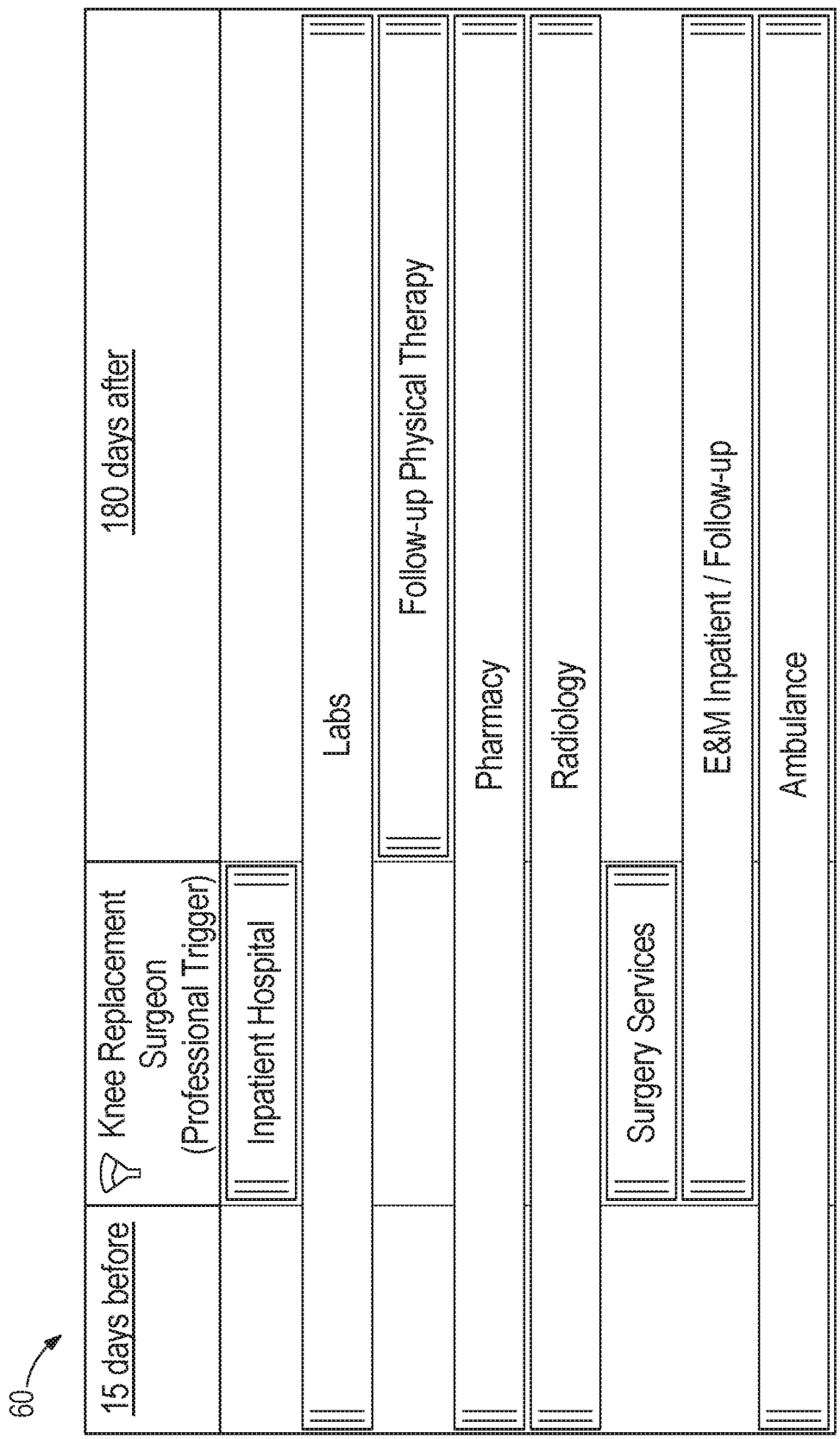

In particular, as illustrated in FIG. 8, if the user wants to add a claim category to the acute episode of care definition that represents all claims relating to the CABG surgeon, the user can use the GUI 60 to select an icon labeled "CABG Surgeon" from the list 64 and drop the icon into one of the windows 62a, 62b, and 63c. In some embodiments, the windows 62a, 62b, and 62c operate like the trigger drop area 66 defined above and change appearance to signal when an icon can be dropped into the window. As illustrated in FIGS. 9a and 9b, the user can add one or more claim categories to the episode of care.

In some embodiments, the user also select options for each claim category added to the episode of care (at 72). The options can include a time period for the claim category. The time period can be used to further filter claims added to the episode. For example, a "Physical Therapy" claim category can be added to the definition of an episode of care to indicate that claims relating to physical therapy should be added to the episode. However, a time period can be associated with the claim category to limit claims added to the episode to only physical therapy claims occurring within the time period (e.g., after the end of the trigger event). For example, when the user drops an icon into one of the windows 62a, 62b, and 62c to add a claim category, the time period for the category can be initially set to the same time period as the selected window. For example, if the before window 62b is set to 30 days before the start of the trigger event, a claim category dropped in the before window 62b defaults to a time period of 30 days before the start of the trigger event. The user, however, can use the GUI 60 to modify the time period for a claim category. In particular, as illustrated in FIG. 9a, the user can select a handle 82 on either side of claim category (e.g., the double lines on each end of a category) to expand or reduce the size of the category, which correspondingly adjusts the time period of the category. In other embodiments, the user can select a category within the timeline 61 (e.g., by double-clicking) to access a pop-up menu that allows the user to select options for the category, such as the time period.

Figure 10A:
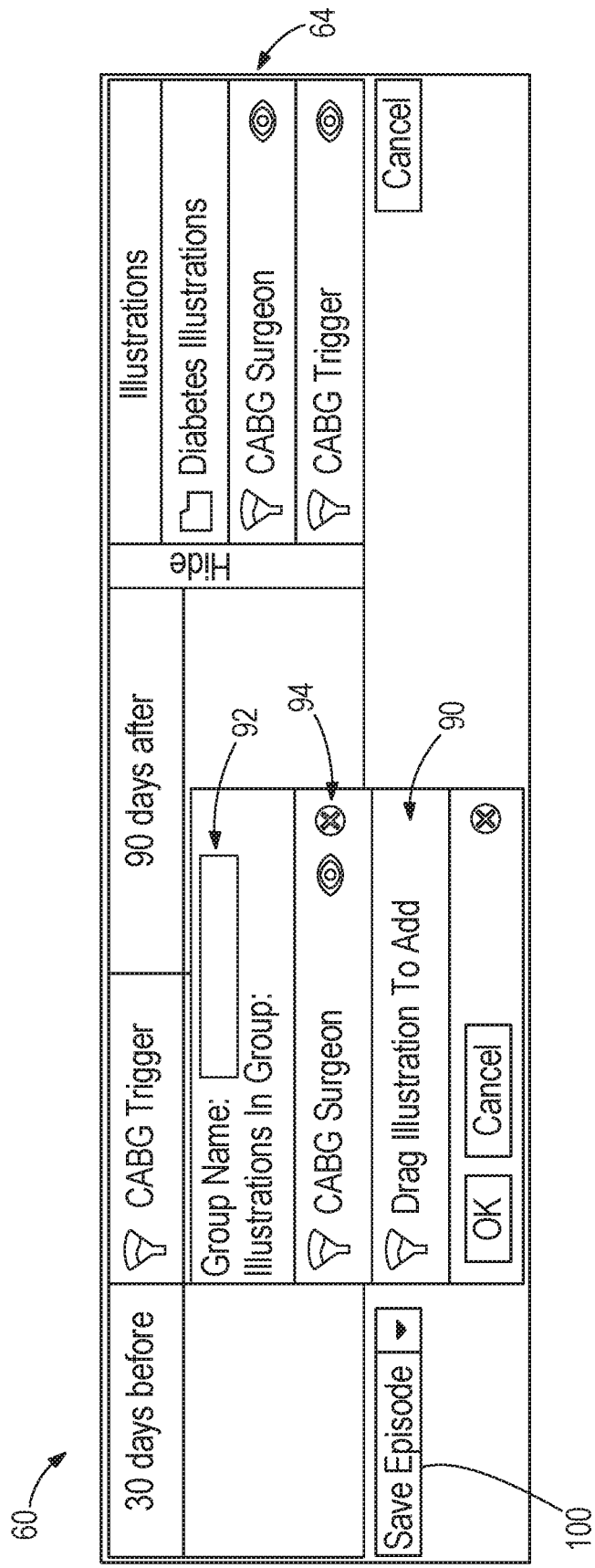
FIGS. 10a and 10b are screen shots illustrating user interfaces for setting options for a claim category included in an episode of care.
Figure 10B:
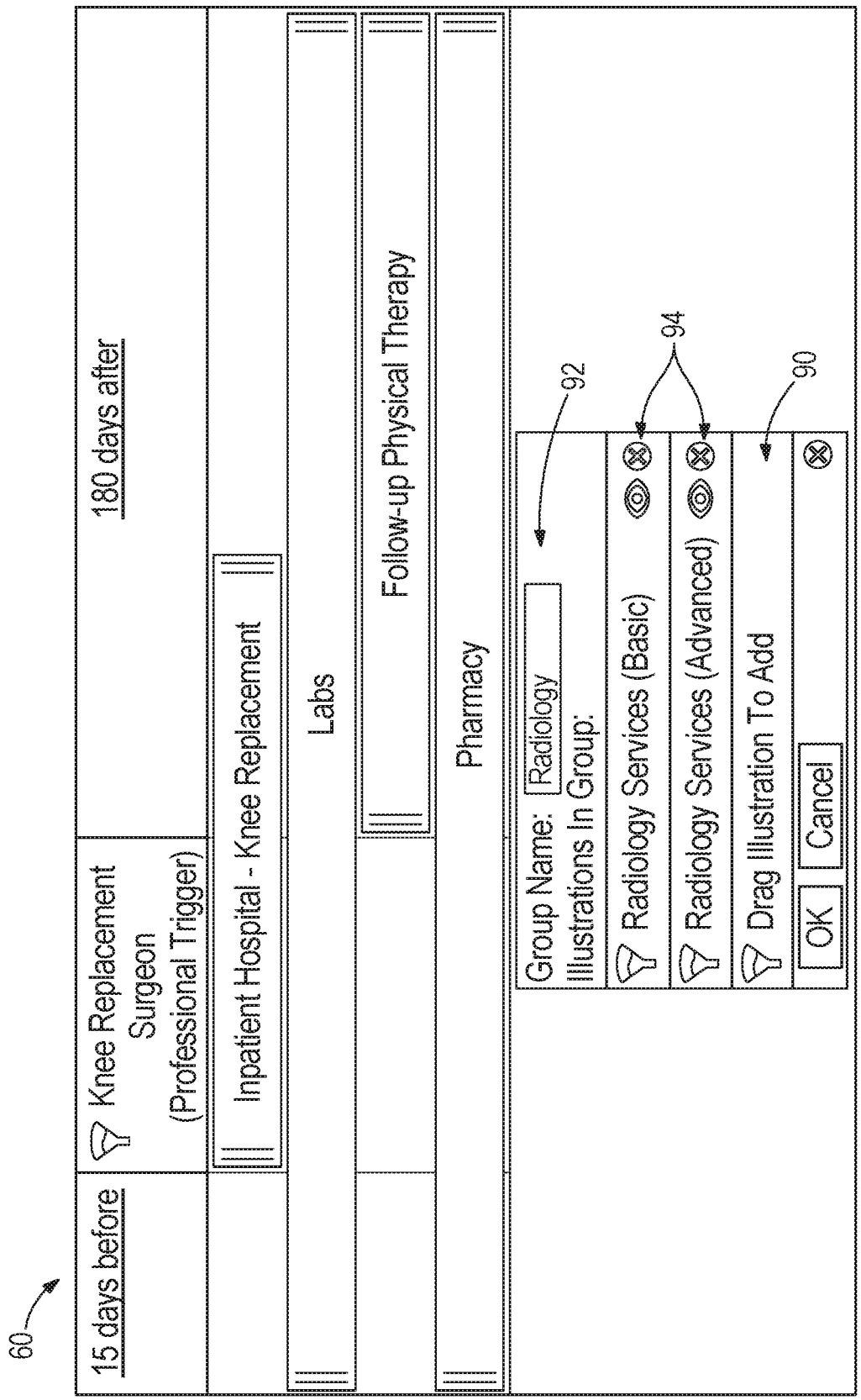

The category options can also include defining sub-categories. For example, as illustrated in FIGS. 10a and 10b, when a user selects a claim category included in the timeline 61 (e.g., by double-clicking the category), the GUI 60 can present the user with one or more input mechanisms for adding additional sub-categories. For example, the GUI 60 can include a sub-category drop area 90. The user can select, drag, and drop additional icons from the list 64 into the area 90 to add sub-categories. In some embodiments, the GUI 60 also includes a name input mechanism 92 that the user can use to input a name for the claim category that represents all of the sub-categories. For example, as illustrated in FIG. 10b, the user can use the GUI 60 to initially add a "Radiology Services (Basic)" claim category to the timeline 61. The user can then add a "Radiology Services (Advanced)" claim category to the previously-added "Radiology Services (Basic)" claim category using the sub-category drop area 90. The user can also name the collection of categories as "Radiology" using the name input mechanism 92. The "Radiology Services (Basic)" category and the "Radiology Services (Advance)" category would be considered sub-categories of the user-defined "Radiology" category. As illustrated in FIGS. 10a and 10b, the user can also use the GUI 60 to remove sub-categories from a claim category (e.g., using a remove or delete selection mechanism 94).

The options for the claim categories can also include filtering logic as described above with respect to the trigger event. The filtering logic can impose additional requirements on the claim categories, such as requiring a predetermined number of claims within the category before any of the claims are added, requiring a predetermined relationship between a claim within the category and one or more claims within or outside of the category, a predetermined bill amount, etc. In some embodiments, a user can select the filtering logic for a claim category from list 64 and drag the selected icon to a claim category already added to the timeline 61.

As illustrated in FIG. 10a, when the user finishes defining the acute episode of care (i.e., selecting a trigger event, setting window time periods, and adding claim categories and associated options), the user can select a "Save" selection mechanism 100 to save the user-set definitions. As described in more detail below, the episode definition application 19a uses the user selections to generate a set of parameters defining an episode of care. The parameters can be applied by to medical claims to group the claims into episodes of care.

Figure 11:
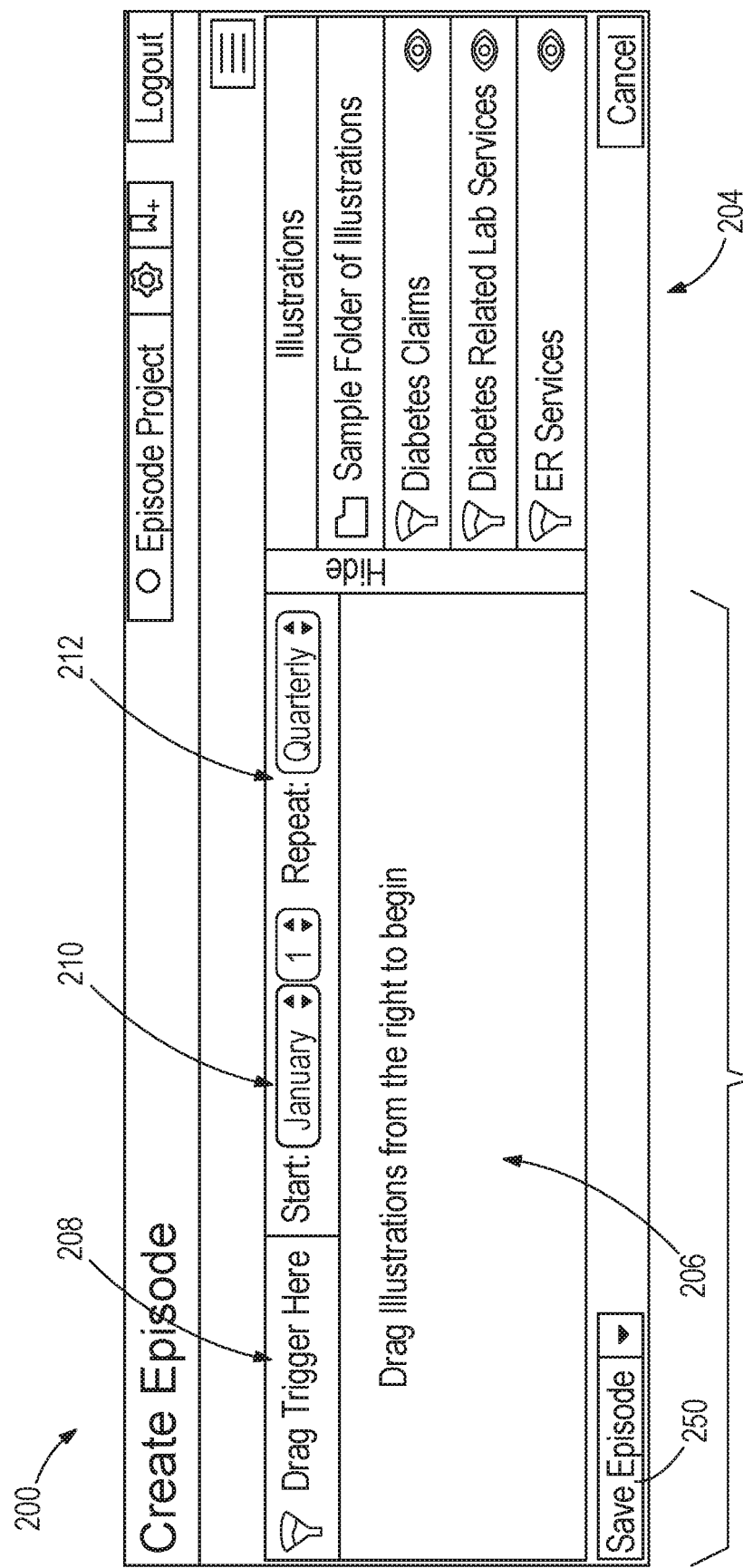
FIG. 11 is a screen shot illustrating a user interface for creating a chronic episode of care.

Returning to FIG. 5a, if the user selects to manually-define a chronic episode of care (at 54), the application 19a generates a GUI that displays options to the user for defining a chronic episode of care. For example, FIG. 11 illustrates a portion of a GUI 200 for defining a chronic episode of care. As illustrated in FIG. 11, similar to the GUI 60, the GUI 200 provides a graphical timeline 201 for defining a chronic episode of care and allows a user to modify the time period of the timeline 201 or portions thereof, add a trigger event to the timeline 201, and add one or more claim categories to the timeline 201. In particular, the user can use the GUI 200 to select a trigger event for the chronic episode of care (at 202, FIG. 5b). For example, as described above for the acute episode of care, in some embodiments, the GUI 200 allows the user to select (e.g., click on) an icon from a list 204 of available claim types and drag the selected icon to a trigger drop area 208.

As noted above, a chronic episode of care is also associated with a time period, and the user can set this time period through the GUI 200 (at 209). In particular, as illustrated in FIG. 11, the timeline 201 includes a window 206 representing the time period of the episode of care. The time period for the window 206 is defined in terms of a start time and a repeat period. Accordingly, the GUI 202 includes a start time selection mechanism 210 and a repeat period selection mechanism 212 (see FIG. 11). The user uses the start time selection mechanism 210 to select a month and day of the month representing the start time for the episode. Similarly, the user uses the repeat period selection mechanism 212 to select a repeat period, such as daily, weekly, monthly, quarterly, annually, etc.

Figure 12:
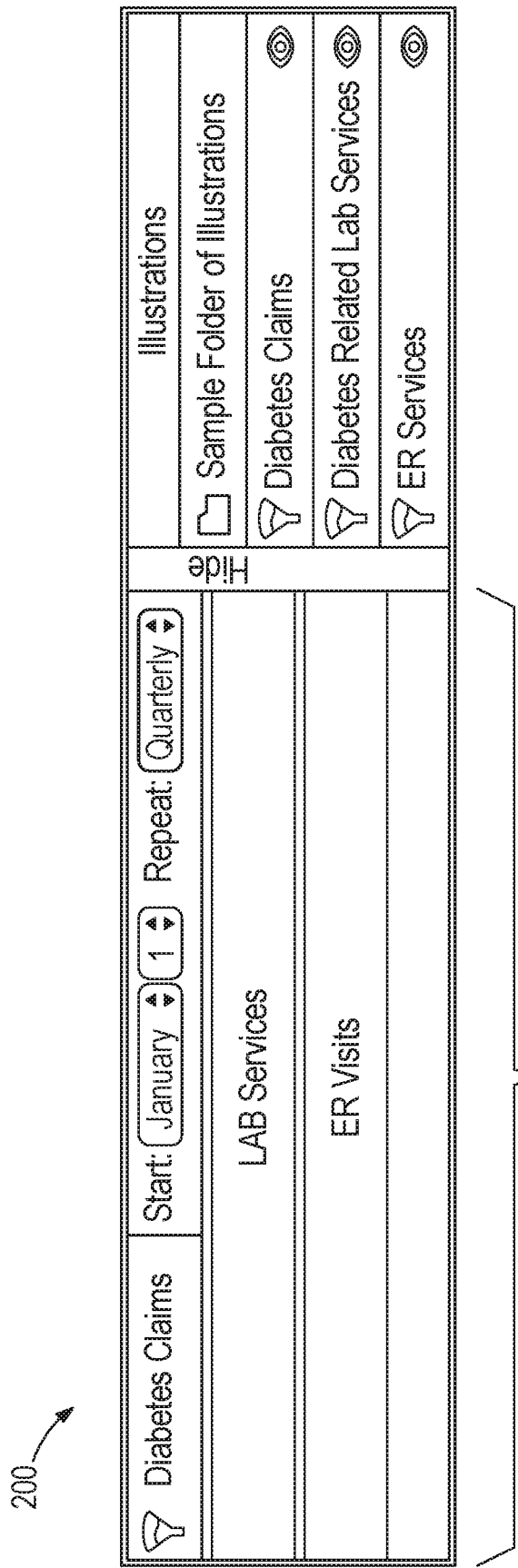
FIG. 12 is a screen shot illustrating a user interface displaying a chronic episode of care including a plurality of claim categories.

Similar to the GUI 60, the GUI 200 also allows a user to add claim categories to the timeline 201 by clicking and dragging an icon from the list 204 into the window 206 (at 240). For example, FIG. 12 illustrates a portion of the GUI 200 that displays the timeline 201 including a plurality of claim categories. Similar to the GUI 60 described above, the GUI 200 can also allow the user to set options for a claim category (at 242). For example, a user can add sub-categories to a timeline 201 as described above with respect to the acute episode of care. As illustrated in FIG. 11, when the user finishes defining the chronic episode of care, the user can select a "Save" selection mechanism 250 to save the user-set definitions.

Figure 5C:
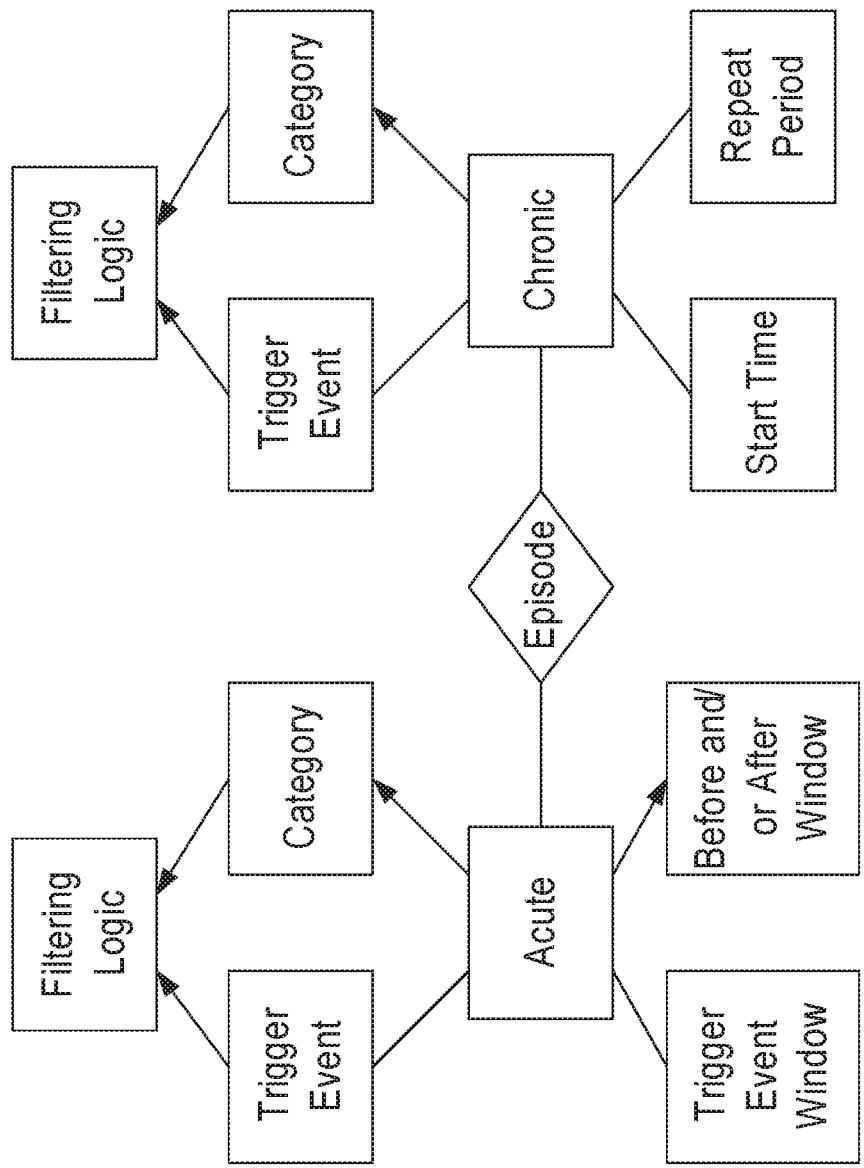
FIG. 5c schematically illustrates components and characteristics of an episode of care.

Returning to FIG. 5b, the episode definition application 19a uses all of the user's selections through the GUI (e.g., for acute and/or chronic episodes) to generate a set of parameters for one or more episodes of care (at 300). For example, as illustrated in FIG. 5c, an episode of care can be defined as either an acute episode or a chronic episode. An acute episode includes as parameters a trigger event window and at least one before window and/or at least one after window. A chronic episode includes as parameters a start date and a repeat period. As illustrated in FIG. 5c, each episode of care also includes as parameters a trigger event and one or more claim categories. Each trigger event and each claim category can be associated with filtering logic. Accordingly, the episode definition application 19a can create parameters for the episode of care defined by the user to create a set of parameters for the episode as illustrated in FIG. 5c. It should be understood that FIG. 5c only provides one way of defining or structuring parameters for a definition of an episode of care and other configurations are possible.

The parameters are applied to medical claims to group claims into appropriate episodes. For example, the processing unit 12 can execute the episode builder application 19b to receive a plurality of medical claims (e.g., from the one or more claim sources 24 and/or from the medium 14) (at 302) and apply the parameters to the plurality of claims to groups the claims (at 304). In particular, the episode builder application 19b can be configured to identify claims matching the trigger event of an episode definition and group the claim matching the trigger event with related claims based on the manually-defined parameters (e.g., based on the time periods associated with the one or more windows of the episode definition and the claim categories included in the episode definition).

In particular, when applying the parameters to the medical claims, the episode builder application 19b can employ one or more rules for creating an episode and grouping claims within an episode. For example, in some embodiments, the episode builder applies three rules when grouping claims into an episode. A first rule is that an episode only exists if a trigger event associated with the episode definition is present. For example, without a surgery claim there is no surgery episode of care. In the case of chronic episodes, an episode only exists if a trigger event is present during the time period associated with the episode definition. A second rule is that the claims included an episode must all be for the same patient. For example, a surgery claim from John Smith should not be combined in an episode with a readmission claim for Susan Smith. A third rule is that claims are only included in an episode of care if the claim falls with the applicable time period associated with the episode definition. For example, a readmission claim seven months after a surgery claim will not be added to the surgery episode if the after window defined for the episode is 180 days.

After the claim data is grouped into an episode of care, the episode of care can be processed to process the claims included in the episode of care. It should also be understood that the episodes of care can be processed or analyzed for other purposes than claim processing. For example, an episode of care can be analyzed to track efficiency, make predictions of further health issues or concerns, perform automatic scheduling for future visits, procedures, laboratory work, etc., review physicians, clinics, or organizations, etc.

Thus, embodiments of the invention provide, among other things, systems and methods for allowing users to manually-define episodes of care. The episode definitions can then be applied to medical claims to group claims into episodes of care for processing. As noted above, by manually-defining episodes, organizations are able to more rapidly (and more cost-effectively) transition to new standards or define episodes that do not necessarily conform to established standards. User-definition of episodes also increases transparency and efficiency. Furthermore, it should be understood that users can use the episode definition application 19a and the associated GUI to update previously-created episode definitions in addition to creating new episode definitions.

It should be understood that the episodes of care can be defined by the user to group data other than medical claims. For example, the user can define an episode to group patient health record data (e.g., procedure data, drug data, etc.), bill and payment data, and any other data associated with a particular patient. Furthermore, as noted above, it should be understood that the systems and methods described above can be used outside of the medical claim industry. For example, the disclosed methods and systems can be used to allow users to define groups for any type of time-based data. In particular, the disclosed systems and methods can be used to group other types of claim data (e.g., worker compensation data, casualty and/or property insurance claims, etc.), sales transaction data, transportation data (e.g., event records associated with buses, trains, airplanes, etc.), message data (e.g., text, email, and/or voice messages), etc. In general, the systems and methods disclosed herein can be used to allow a user to manually define parameters for related data sets that should be collected or processed as a group or collection rather than individually.

For example, the methods and systems disclosed herein can be used to group retail sales data. In this situation, the trigger event can include a life event of a consumer, such as the birth of a baby or the moving to a new apartment or house. The episode of activity associated with the trigger event would include and track related purchases before and/or after the trigger event. In particular, for a moving trigger event, the event could be defined as the purchase of one or more house-ware items (e.g., dishes, furnishings, appliances, etc.) or the purchase of moving services. The episode of activity could then track all purchases occurring within a predetermined time period (e.g., one year). The episode of activity could then be processed or analyzed to identify the purchasing habits of newly independent people, which provides valuable marketing information for retailers.

Similarly, the methods and systems disclosed herein can be used to group maintenance repairs for a fleet of vehicles. For example, a trigger event can include a major repair on a vehicle, and the episode of activity including the trigger event can include future related maintenance. In particular, after repairing a vehicle transmission, additional repairs may be necessary to address incorrect alignment of the transmission or other problems relating to the transmission repair. The episode of activity could then be processed or analyzed to better understand the cost impacts of repairs.

The methods and systems disclosed herein can also be used to create vacation or travel bundles. For example, a trigger event can include a scheduled trip by an individual (e.g., by plane, train, bus, boat, etc.), the episode of activity including the trigger event can include all other trips taken by the individuals within a period of time before and/or after the trigger event. Accordingly, travel agencies can analyze the episodes of activity to identify travel packages to offer. Similarly, government agencies can analyze the episodes of care to assess mass transit (e.g., add or removing routes) by better understanding how individuals combined modes of transportation to reach a particular destination.

Furthermore, the methods and systems described here can be used to track a product development cycle. For example, the trigger event can include a product making it to market, and the associated episode of activity can include all events leading up to the trigger event (e.g., designing, testing, manufacturing, packaging, etc.). Analyzing the episodes of activity provides a better understanding of important costs and timelines for successfully delivering a product to market.

In all of the above examples, a user can use a graphical user interface similar to the examples provided above with respect to medial claim processing to add and modify a graphical timeline to define the parameters for grouping data into an episode of activity. In particular, the user can use a graphical user interface to (i) select a trigger event (and associated filtering logic), (ii) select or modify a time period (e.g., a trigger event window, a before window, and/or an after window); and (iii) add one or more categories (and associated options). The user-defined parameters can then be automatically applied to data to generate the episodes of activities, which can be analyzed and processed in various ways to provide efficient and improved use of data.

Various features of the invention are set forth in the following claims.

What is claimed is:

1. A method of processing medical claims, the method comprising:
   generating, by a processor, a graphical user interface for display to a user on a display communicating with the processor;
   receiving, by the processor, a first selection of a trigger event for an episode of care from the user through the graphical user interface;
   receiving, by the processor, a second selection of a time period for the episode of care from the user through the graphical user interface;

receiving, by the processor, a third selection of a type of claim to include in the episode of care from the user through the graphical user interface;

automatically generating, by the processor, parameters for the episode of care based on the first selection, the second selection, and third selection;

storing the parameters;

receiving the medical claims; and selecting a subset of the medical claims to be included in an instance of the episode of care based on the parameters by identifying a first medical claim included in the medical claims matching the first selection and identifying a second medical claim included in the medical claims matching the third selection and occurring within the second selection.

2. The method of claim 1, wherein receiving the second selection of the at least one time period includes receiving a resizing of at least one element included in the graphical user interface.

3. The method of claim 1, wherein generating the graphical user interface includes generating a graphical user interface including a before window defining a time period before a start of the trigger event and an after window defining a time period after the end of the trigger event.

4. The method of claim 3, wherein receiving the third selection of the type of claim includes receiving a position of an icon within one of the before window and the after window.

5. The method of claim 3, wherein receiving the second selection of the time period includes receiving a resizing of one of the before window and the after window.

6. The method of claim 1, wherein receiving the selection of the time period includes receiving a selection of a time period occurring prior to the trigger event.

7. The method of claim 1, wherein receiving the selection of the time period includes receiving a selection of a time period occurring after the trigger event.

8. The method of claim 1, wherein receiving the selection of the time period includes receiving a selection of a plurality of time periods occurring prior to the trigger event.

9. The method of claim 1, wherein receiving the selection of the time period includes receiving a selection of a plurality of time periods occurring after the trigger event.

10. The method of claim 1, wherein receiving the second selection of the time period includes receiving a selection of a start time and a repeat period.

11. The method of claim 1, further comprising receiving a fourth selection of a time period associated with the third selection of the type of claim from the user through the graphical user interface.

12. A system for processing medical claims, the system comprising:
a computing device including
non-transitory computer readable medium storing at least one application, and
a processor configured to execute the at least one application to:
generate a graphical user interface for display to a user,
receive a first selection of a trigger event for a group of claims from the user through the graphical user interface,
receive a second selection of a plurality of time periods for the group of claims from the user through the graphical user interface, wherein each of the plurality of time periods occurs prior to the trigger event or wherein each of the plurality of time periods occurs after the trigger event,
receive a third selection of a type of claim to include in the group of claims from the user through the graphical user interface,
automatically generate parameters for the group of claims based on the first selection, the second selection, and the third selection,
store the parameters,
receive the medical claims, and
select a subset of the medical claims to be included in an instance of the group of claims based on the parameters by identifying a first medical claim included in the medical claims matching the first selection and identifying a second medical claim included in the medical claims matching the third selection and occurring, with respect to the first medical claim, within one of the plurality of time periods of the second selection.

13. The system of claim 12, wherein the graphical user interface allows the user to associate the third selection of the type of claim with at least one of the plurality of time periods.

14. The system of claim 12, wherein the graphical user interface allows the user to make the second selection by resizing an element included in the graphical user interface.

15. The system of claim 12, wherein the graphical user interface includes at least one selected from a group consisting of a before window occurring before a start of the trigger event and an after window occurring after the end of the trigger event and wherein the graphical user interface allows user to make the third selection by positioning an icon in at least one of the before window and the after window.

16. A system for processing medical claims, the system comprising:
a computing device including
non-transitory computer readable medium storing at least one application, and
a processor configured to execute the at least one application to:
generate a graphical user interface for display to a user,
receive a first selection of a trigger event for a group of claims from the user through the graphical user interface,
receive a second selection of a first plurality of time periods for the group of claims from the user through the graphical user interface, wherein each of the first plurality of time periods occurs before the trigger event,
receive a third selection of a second plurality of time periods for the group of claims from the user through the graphical user interface, wherein each of the second plurality of time periods occurs after the trigger event,
receive a fourth selection of a type of claim to include in the group of claims from the user through the graphical user interface,
automatically generate parameters for the group of claims based on the first selection, the second selection, the third selection, and the fourth selection,
store the parameters,
receive the medical claims, and
select a subset of the medical claims to be included in an instance of the group of claims based on the parameters by identifying a first medical claim included in the medical claims matching the first selection and identifying a second medical claim included in the medical claims matching the fourth selection and occurring, with respect to the first medical claim, within one of the first plurality of time periods of the second selection or within one of the second plurality of time periods of the third selection.

17. The system of claim 16, wherein the graphical user interface includes a window associated with each of the first plurality of time periods of the second selection and a window associated with each of the second plurality of time periods of the third selection.

18. The system of claim 17, wherein the window associated with each of the first plurality of time periods is resizable.

19. The system of claim 17, wherein the window associated with each of the second plurality of time periods is resizable.

20. The system of claim 16, wherein the graphical user interface allows a user to associate the fourth selection of the type of claim with one of the first plurality of time periods or one of the second plurality of time periods.

* * * * *